United States Patent [19]
Edery et al.

[11] Patent Number: 5,843,683
[45] Date of Patent: Dec. 1, 1998

[54] PAS DOMAIN PROTEINS

[75] Inventors: Isaac Edery, Brookline; Zuoshi Josh Huang, Waltham; Michael Rosbash, Newton, all of Mass.

[73] Assignee: Brandeis University, Waltham, Mass.

[21] Appl. No.: 716,630

[22] Filed: Sep. 23, 1996

Related U.S. Application Data

[63] Continuation of Ser. No. 531,097, Sep. 20, 1995, abandoned, which is a continuation of Ser. No. 91,841, Jul. 14, 1993, abandoned.

[51] Int. Cl.$^6$ .................. G01N 33/566; C07K 14/705; C12Q 1/68
[52] U.S. Cl. .................. 435/7.8; 435/6; 435/7.1
[58] Field of Search .................. 435/6, 7.1, 7.8; 514/2; 530/300, 345, 350, 402

[56] References Cited

FOREIGN PATENT DOCUMENTS 9213091  1/1992  WIPO.

OTHER PUBLICATIONS

Ema et al. (1992) Biochem Biophys Res. Comm 184(1)246–53.
Granowitz et al. (1992) Blood 79(9), 2356–2363.
Fields et al. (1989) Nature 340, 245–246.
Hadley et al. (1988) J. Inher. Metab, Dis. 11, 387–396.
Marks et al. (1992) EMBO J. 11(4), 1419–1435.
Nambu et al. (1991) Cell 67, 1157–1167.
M. Rosbash and J.C. Hall, "The Molecular Biology of Circadian Rhythms," Neuron, vol. 3, pp. 387–398, 1989.
R.J. Konopka and S. Benzer, "Clock Mutants of *Drosophila Melanogaster*," Proc. Nat. Acad. Sci. USA, vol. 68, No. 9, pp. 2112–2116, 1971.
E.C. Hoffman et al., "Cloning of a Factor Required for Activity of the Ah (Dioxin) Receptor," Science, vol. 252, pp. 954–958, 1991.
P. Reddy et al., "The Period Clock Locus of *D. Melanogastere* Codes for a Proteoglycan," Cell, vol. 46, pp. 53–61, 1986.
X. Liu et al., "The Period Gene Encodes a Predominantly Nuclear Protein in Adult Drosophila," The Journal of Neuroscience, pp. 2735–2744, 1992.
S.T. Crews et al., "The Drosophila Single–Minded Gene Encodes a Nuclear Protein with Sequence Similarity to the Per Gene Product," Cell, vol. 52, pp. 143–151, 1988.
K.M. Burbach et al., "Cloning of the Ah–Receptor cDNA Reveals a Distinctive Ligand–Activated Transcription Factor," Proc. Natl. Acad. Sci. USA, vol. 89, pp. 8185–8189, 1992.

*Primary Examiner*—George C. Elliott
*Assistant Examiner*—Thomas G. Larson
*Attorney, Agent, or Firm*—Lyon & Lyon LLP

[57] ABSTRACT

A novel conserved amino acid motif ("PAS") which provides a binding site for homo and hetero protein interactions has been found in mammalian and insect proteins. Abnormalities in these protein interactions are believed to be responsible for a variety of human diseases or conditions, including behavioral disorders and epithelial tissue cancers. Methods for identifying persons who have a disposition towards these behavioral disorders or epithelial tissue cancers are described. Methods are also described for identifying agonists and antagonists of proteins or related peptides containing PAS domains. Screening such agents involves assessing the ability of candidate compounds to promote or interfere with the binding of certain biologic preparations comprised of PAS-containing proteins. Successful agonists or antagonists should be useful in modifying the effects of human behavioral disorders, as well as certain epithelial cancers.

5 Claims, 6 Drawing Sheets

SEQUENCE LISTING ( 1 ) GENERAL INFORMATION:

( i i i ) NUMBER OF SEQUENCES: 9

( 2 ) INFORMATION FOR SEQ ID NO: 1:

( i ) SEQUENCE CHARACTERISTICS:
        ( A ) LENGTH: 6 amino acids
        ( B ) TYPE: amino acid
        ( D ) TOPOLOGY: linear     ( i i ) MOLECULE TYPE: Protein     ( v ) FRAGMENT TYPE: Internal Fragment     ( v i ) ORIGINAL SOURCE:
        ( A ) ORGANISM: Human
        ( G ) CELL TYPE: Hepatoma
        ( H ) CELL LINE: HepG2

( x ) PUBLICATION INFORMATION:
        ( A ) AUTHORS: Hoffman, E.C., H. Reyes,
            F.-F. Chu, F. Sander,
            L.H. Conley, B.A. Brooks,
            and O. Hankinson
        ( B ) TITLE: CLONING OF A FACTOR REQUIRED
            FOR ACTIVITY OF THE Ah (DIOXIN)
            RECEPTOR
        ( C ) JOURNAL: Science
        ( E ) ISSUE: 252
        ( F ) PAGES: 954-958
        ( G ) DATE: May 17, 1991
        ( K ) RELEVANT RESIDUES IN SEQ ID NO: from
            240- 245

( x i ) SEQUENCE DESCRIPTION: SEQ ID NO: 1:

Phe  Val  Leu  Val  Val  Thr
        1                          5

( 2 ) INFORMATION FOR SEQ ID NO: 2:

( i ) SEQUENCE CHARACTERISTICS:
        ( A ) LENGTH: 9 amino acids
        ( B ) TYPE: amino acid
        ( D ) TOPOLOGY: linear     ( i i ) MOLECULE TYPE: Protein     ( v ) FRAGMENT TYPE: Internal Fragment     ( v i ) ORIGINAL SOURCE:
        ( A ) ORGANISM: Human
        ( G ) CELL TYPE: Hepatoma
        ( H ) CELL LINE: HepG2

( x ) PUBLICATION INFORMATION:
        ( A ) AUTHORS: Hoffman, E.C., H. Reyes,
            F.-F. Chu, F. Sander,
            L.H. Conley, B.A. Brooks,
            and O. Hankinson
        ( B ) TITLE: CLONING OF A FACTOR REQUIRED
            FOR ACTIVITY OF THE Ah (DIOXIN)
            RECEPTOR
        ( C ) JOURNAL: Science
        ( E ) ISSUE: 252
        ( F ) PAGES: 954-958
        ( G ) DATE: May 17, 1991
        ( K ) RELEVANT RESIDUES IN SEQ ID NO: from
            412- 420

( x i ) SEQUENCE DESCRIPTION: SEQ ID NO: 2:

Leu  Gly  Tyr  Thr  Glu  Val  Glu  Leu  Cys
        1                          5

( 2 ) INFORMATION FOR SEQ ID NO: 3:

( i ) SEQUENCE CHARACTERISTICS:
        ( A ) LENGTH: 6 amino acids
        ( B ) TYPE: amino acid
        ( D ) TOPOLOGY: linear    ( i i ) MOLECULE TYPE: Protein     ( v ) FRAGMENT TYPE: Internal Fragment   ( v i ) ORIGINAL SOURCE:
        ( A ) ORGANISM: Drosophila     ( x ) PUBLICATION INFORMATION:
        ( A ) AUTHORS: Crews, S.T., J.B. Thomas,
            and C.S. Goodman
        ( B ) TITLE: THE DROSOPHILA SINGLE- MINDED
            GENE ENCODES A NUCLEAR PROTEIN
            WITH SEQUENCE SIMILARITY TO THE
            PER GENE PRODUCT
        ( C ) JOURNAL: Cell
        ( E ) ISSUE: 52
        ( F ) PAGES: 143-152
        ( G ) DATE: January 15, 1988
        ( K ) RELEVANT RESIDUES IN SEQ ID NO: from
            240- 245

( x i ) SEQUENCE DESCRIPTION: SEQ ID NO: 3:

```
          Phe   Ile   Phe   Val   Val   Ala
          1                       5
```

( 2 ) INFORMATION FOR SEQ ID NO: 4:

( i ) SEQUENCE CHARACTERISTICS:
        ( A ) LENGTH: 9 amino acids
        ( B ) TYPE: amino acid
        ( D ) TOPOLOGY: linear    ( i i ) MOLECULE TYPE: Protein     ( v ) FRAGMENT TYPE: Internal Fragment   ( v i ) ORIGINAL SOURCE:
        ( A ) ORGANISM: Drosophila     ( x ) PUBLICATION INFORMATION:
        ( A ) AUTHORS: Crews, S.T., J.B. Thomas,
            and C.S. Goodman
        ( B ) TITLE: THE DROSOPHILA SINGLE- MINDED
            GENE ENCODES A NUCLEAR PROTEIN
            WITH SEQUENCE SIMILARITY TO THE
            PER GENE PRODUCT
        ( C ) JOURNAL: Cell
        ( E ) ISSUE: 52
        ( F ) PAGES: 143-152
        ( G ) DATE: January 15, 1988
        ( K ) RELEVANT RESIDUES IN SEQ ID NO: from
            412- 420

( x i ) SEQUENCE DESCRIPTION: SEQ ID NO: 4:

```
          Thr   Gly   Tyr   Glu   Pro   Gln   Asp   Leu   Ile
          1                       5
```

( 2 ) INFORMATION FOR SEQ ID NO: 5:

( i ) SEQUENCE CHARACTERISTICS:
        ( A ) LENGTH: 6 amino acids
        ( B ) TYPE: amino acid
        ( D ) TOPOLOGY: linear    ( i i ) MOLECULE TYPE: Protein     ( v ) FRAGMENT TYPE: Internal Fragment ( v i ) ORIGINAL SOURCE:
  ( A ) ORGANISM: Mouse
  ( G ) CELL TYPE: Hepatoma
  ( H ) CELL LINE: Hepa 1c1c7

( x ) PUBLICATION INFORMATION:
  ( A ) AUTHORS: Burbach, K.M., A. Poland,
    and C.A. Bradfield
  ( B ) TITLE: CLONING OF THE Ah- RECEPTOR cDNA
    REVEALS A NOVEL LIGAND ACTIVATED
    TRANSCRIPTION FACTOR
  ( C ) JOURNAL: Proc. Natl. Acad. Sci. USA
  ( E ) ISSUE: 89
  ( F ) PAGES: 8185-8189
  ( G ) DATE: September, 1992
  ( K ) RELEVANT RESIDUES IN SEQ ID NO: from
    240- 245

( x i ) SEQUENCE DESCRIPTION: SEQ ID NO: 5:

```
Phe  Leu  Phe  Ile  Val  Ser
1                   5
```

( 2 ) INFORMATION FOR SEQ ID NO: 6:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: Protein ( v ) FRAGMENT TYPE: Internal Fragment ( v i ) ORIGINAL SOURCE:
    ( A ) ORGANISM: Mouse
    ( G ) CELL TYPE: Hepatoma
    ( H ) CELL LINE: Hepa 1c1c7

( x ) PUBLICATION INFORMATION:
    ( A ) AUTHORS: Burbach, K.M., A. Poland,
      and C.A. Bradfield
    ( B ) TITLE: CLONING OF THE Ah- RECEPTOR cDNA
      REVEALS A NOVEL LIGAND ACTIVATED
      TRANSCRIPTION FACTOR
    ( C ) JOURNAL: Proc. Natl. Acad. Sci. USA
    ( E ) ISSUE: 89
    ( F ) PAGES: 8185-8189
    ( G ) DATE: September, 1992
    ( K ) RELEVANT RESIDUES IN SEQ ID NO: from
      412- 420

( x i ) SEQUENCE DESCRIPTION: SEQ ID NO: 6:

```
Val  Gly  Tyr  Gln  Pro  Gln  Glu  Leu  Ile
1                        5
```

( 2 ) INFORMATION FOR SEQ ID NO: 7:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: Protein ( v ) FRAGMENT TYPE: Internal Fragment ( v i ) ORIGINAL SOURCE:
    ( A ) ORGANISM: Drosophila ( x ) PUBLICATION INFORMATION:
    ( A ) AUTHORS: Reddy, P., A.C. Jacquier,
      N. Abovich, G. Petersen, and
      M. Rosbash
    ( B ) TITLE: THE PERIOD CLOCK LOCUS OF D.
      MELANOGASTER CODES FOR A PROTEOGLYCAN
(C) JOURNAL: Cell
(E) ISSUE: 46
(F) PAGES: 53-61
(G) DATE: 1986
(K) RELEVANT RESIDUES IN SEQ ID NO: from
240- 245

(xi) SEQUENCE DESCRIPTION: SEQ ID NO: 7:

```
Phe  Cys  Cys  Val  Ile  Ser
1                      5
```

(2) INFORMATION FOR SEQ ID NO: 8:

(i) SEQUENCE CHARACTERISTICS:
      (A) LENGTH: 9 amino acids
      (B) TYPE: amino acid
      (D) TOPOLOGY: linear   (ii) MOLECULE TYPE: Protein    (v) FRAGMENT TYPE: Internal Fragment   (vi) ORIGINAL SOURCE:
      (A) ORGANISM: Drosophila    (x) PUBLICATION INFORMATION:
      (A) AUTHORS: Reddy, P., A.C. Jacquier,
          N. Abovich, G. Petersen, and
          M. Rosbash
      (B) TITLE: THE PERIOD CLOCK LOCUS OF D.
          MELANOGASTER CODES FOR A
          PROTEOGLYCAN
      (C) JOURNAL: Cell
      (E) ISSUE: 46
      (F) PAGES: 53-61
      (G) DATE: 1986
      (K) RELEVANT RESIDUES IN SEQ ID NO: from
          412- 420

(xi) SEQUENCE DESCRIPTION: SEQ ID NO: 8:

```
Leu  Gly  Tyr  Leu  Pro  Gln  Asp  Leu  Ile
1                      5
```

(2) INFORMATION FOR SEQ ID NO: 9:

(i) SEQUENCE CHARACTERISTICS:
      (A) LENGTH: 11 amino acids
      (B) TYPE: amino acid
      (D) TOPOLOGY: linear   (ii) MOLECULE TYPE: Protein    (v) FRAGMENT TYPE: Internal Fragment   (vi) ORIGINAL SOURCE:
      (A) ORGANISM: Influenza    (x) PUBLICATION INFORMATION:
      (A) AUTHORS: P.A. Kolodziej and R.A. Young
      (B) TITLE: EPITOPE TAGGING AND PROTEIN
          SURVEILLANCE
      (C) JOURNAL: Methods In Enzymology
      (E) ISSUE: 194
      (F) PAGES: 508-519
      (G) DATE: 1991

(xi) SEQUENCE DESCRIPTION: SEQ ID NO: 9:

```
Tyr  Pro  Tyr  Asp  Val  Pro  Asp  Val  Ala  Ser  Leu
1                      5                        10
```

PAS DOMAIN PROTEINS

This application is a continuation of application Ser. No. 08/531,097, filed Sep. 20, 1995, now abandoned, which is a continuation of application Ser. No. 08/091,841, filed Jul. 14, 1993, now abandoned.

TECHNICAL FIELD

This invention relates to methods for identifying and treating certain behavioral disorders and cancers, and drugs useful in such treatment.

BACKGROUND OF THE INVENTION

Daily fluctuations in physiological and behavioral processes are governed by an endogenous circadian (approximately 24 h) pacemaker or clock. While the mechanisms which underlie circadian rhythms are not well understood in humans, it is believed that certain gene products are required for the proper manifestation of circadian rhythms.

Arguably, the best known "rhythm gene" at present is the product of the period locus (per) of Drosophila melanogaster. This gene product contains a ca. 270 amino acid motif called PAS. Nambu, J. R., et al., Cell (1991); 67:1157–1167. A PAS motif is also contained in two proteins critical to the aryl hydrocarbon ("AH") receptor system in the liver and lung that converts environmental carcinogens (e.g. dioxin, cigarette smoke) into carcinogenic compounds. Evidence exists in mice that inheritance of the AH receptor is involved in the adverse response to carcinogens and a genetic predisposition to certain forms of cancer. Knutson, J. D. and A. Poland, Cell (1980); 22:27–36; Knutson, J. C. and A. Poland, Cell (1982); 30:225–234; Poland, A. et al, Nature (1982); 300:271–273. Evidence also exists for this AH receptor system involvement in humans. Kellerman, G. et al, Amer. J. Hum. Genet. (1973); 25:327–331; Paigen, B. et al, Amer. J. Hum. Genet. (1978); 30:561–571; Borresen A. L. et al, Clinical Genetics (1981); 19:281–289.

SUMMARY OF THE INVENTION

Applicants are the first to recognize that abnormalities in PAS domain protein functions may cause certain conditions or diseases in humans, such as human behavioral disorders and epithelial tissue cancers. Thus, the present invention concerns identifying, purifying and characterizing PAS-containing proteins in humans. The present invention also encompasses methods for identifying individuals who may have conditions or diseases influenced by abnormalities in PAS-containing protein functions. Further, the present invention concerns methods for identifying physiologically active materials useful to treat these diseases by assessing the ability of these materials to promote or interfere with naturally occurring, isolated or cloned PAS-containing protein complexes.

The best characterized clock gene candidate is the period (per) gene in the fruit fly, Drosophila melanogaster. Mutations in the Per gene can shorten, lengthen or essentially abolish the circadian rhythms of the fruit fly. Konopka, R. J. and S. Benzer, Proc. Natl. Acad. Sci. USA, (1971); 68:2112–2116; Rosbash, M. and J. C. Hall, Neuron (1989); 3:387–398; Young, M. W., et al., Molecular Biology of the Drosophila clock. In: Neuronal and Cellular Oscillators, edited by Jacklet, J. W. New York: Marcel Dekker, 1989, p. 529–542.

Recent findings by applicants indicate that the per gene product (PER) is involved in a feed-back loop that influences the circadian transcription of its own gene. The transcription of per is inversely correlated to the apparent concentration of PER present in those cells that express the per gene. The concentration of PER is also positively correlated to the fruitfly circadian clock, reaching maximum concentration at approximately two hours before lights on and reaching minimum concentration at approximately two hours before lights out when a twelve hour lights on, twelve-hour lights off cycle is used. This result is consistent with observations in other organisms that the temporal regulation of gene expression is an important feature of the circadian oscillator. Takahashi, J. S., Science (1992); 258:238–240. Although the biochemical function of PER has not been established, a PAS amino acid motif is also present in three basic Helix-Loop-Helix transcription factors (BHLH), specifically, the D. melanogaster single-minded gene product (SIM) and both subunits of the mammalian dioxin receptor complex (AH). Nambu, J. R., et al. Cell (1991) 67:1157–1167; Hoffman, E. C., et al., Science (1991); 252:954–958; Burbach, K. M., et al., Proc. Natl. Acad. Sci. USA (1992); 89:8185–8189.

The aryl hydrocarbon or dioxin receptor complex (AH) is actively expressed in a number of mammalian tissues and cells. In the liver, where the AH complex has been best characterized, the two subunits are known to function as a heterodimer and bind DNA to activate transcription of detoxification genes, such as members of the cytochrome P-450 family. Hoffman, E. C. et al, Science (1991); 252:954–958; Burbach, K. M. et al, Proc. Natl. Acad. Sci. USA (1992); 89:8185–8189; Ema, M. et al, Biochem. Biophys. Res. Commun. (1992); 184:246–253. In the presence of a toxin or ligand, such as aryl hydrocarbons or dioxin, the two subunits dimerize and contribute to initiating biological functions that make the toxins water soluble, so that the toxins can be eliminated from the body. But the heterodimer also activates expression of genes whose products convert toxins into carcinogens. In other words, the PAS-containing proteins are required intermediaries in a necessary detoxification process, but as a consequence also participate in a coupled toxification process.

Applicants have shown in D. melanogaster that the PAS domain of the PER protein functions in vitro as a novel protein dimerization motif, and can mediate associations between different members of the PAS protein family. One implication of this finding is that the PAS motif also functions as a dimerization domain in the three BHLH proteins of known functions. These findings also establish a link between PER and proteins of known biochemical function and indicate that PER itself might affect circadian rhythms by modulating transcription.

The dimerization efficiency of the PER proteins can be decreased by several missense mutations in the PAS domain. In particular, mutating the hydrophobic valine at position 243, which lies in a conserved hydrophobic region just N-terminal to the first PAS repeat, to a hydrophilic aspartic acid results in vitro in a 7 fold decrease in PER self-association efficiency and in vivo in lengthening the fruitfly circadian period from 24 hours to 29 hours. These results indicate a biological mechanism whereby PER may regulate circadian gene transcription by interacting with the PAS domain of BHLH-PAS-containing transcription factors.

Therefore, the invention features methods for identifying and characterizing new proteins in humans that contain the PAS motif and purifying the nucleic acid that encodes these protein(s). The purified nucleic acid may then be introduced into host cells and the PAS-containing proteins expressed in quantities sufficient to characterize the PAS-PAS interactions of the newly identified proteins. Accordingly, once the PAS sequences have been identified and expressed, the PAS sequences can be screened to determine the binding affinity of the PAS-PAS interactions in the presence or absence of various molecules. Such screens can be used to identify therapeutic molecules for treatment of human behavioral disorders, such as seasonal affective disorder, sleep disorders and jet lag, as well as treatment or prevention of toxic molecule build-up to prevent epithelial tissue cancers.

Thus, in the first aspect, the present invention features a method for identifying, isolating and characterizing the activity of PAS-domain containing proteins in humans or other animals which contain PAS domains. The invention also includes methods for identifying, isolating and characterizing the genes that encode PAS-containing proteins. Once a gene encoding a PAS-containing protein is located, it can be cloned, amplified and purified into a substantially pure form. Genes isolated from various individuals can be obtained and sequenced according to these methods. The sequences then can be compared to determine the correlation of DNA sequence abnormalities to behavioral disorders and cancers.

The gene can also be cloned into a plasmid, the plasmid expressed and recombinant protein isolated in substantially pure form, such that large quantities of the protein are available for further investigation. For example, one could also determine the amino acid sequence of PAS-containing proteins from various individuals to find correlations between the amino acid sequence of the PAS-containing protein to behavioral disorders and cancers.

In the second aspect, the invention features an in vitro assay method for identifying, screening and characterizing compounds potentially useful for treatment of diseases or disorders arising from abnormal PAS-PAS binding affinities. This method includes bringing together a test sample and a PAS-containing protein preparation. The test sample contains one or more test compounds, and the PAS-containing protein preparation contains one or more human peptides comprising at least the PAS region being investigated. The test sample is incubated with the PAS-containing protein preparation under conditions that would allow the PAS domain containing proteins to interact in the absence of the test sample. Those test samples containing one or more test compounds that affect PAS-containing protein binding functions can then be identified.

In the third aspect, the invention features an in vivo assay method for identifying, screening and characterizing compounds potentially useful for treatment of diseases or disorders arising from abnormal PAS-PAS binding affinities. The method includes transfecting purified nucleic acid encoding a PAS-containing protein into a host cell which contains, or is manipulated to contain nucleic acid of a reporter gene whose transcription is regulated by the presence or absence of dimerized PAS-containing proteins. Test sample compounds can then be introduced and the effect on reporter gene transcription assayed.

In the fourth aspect, the invention features a method for diagnosis of a disease or condition which is characterized by abnormal PAS-PAS binding affinities. The method includes isolating nucleic acid from a patient, and locating the nucleic acid encoding one or more PAS-containing proteins sought to be investigated. In one preferred embodiment, this nucleic acid can be sequenced and the portion encoding the PAS domain region compared to the nucleic acid sequence of patients with normal PAS-PAS binding affinities. In another preferred embodiment, abnormal nucleic acid can be transfected into a host cell or used in the in vitro assay as described in the preceding paragraphs and the effect on reporter gene transcription or PAS protein interactions can be assayed.

These and other aspects of the invention will be apparent upon review of the detail description of the preferred embodiments.

DESCRIPTION OF THE DRAWINGS

FIG. 2 (B). Wild-type and mutant versions of PER 233–568 fragments were translated in vitro and mixed with PER 233–685/H (FIG. 1A). Single or mixed translation products were analyzed by 12% SDS-PAGE either directly (lanes 1 to 6) or after immunoprecipitation with anti-HA antibody (lanes 7–14). The positions of PER 233–685/H (upper right) and PER 233–568 (lower right) are indicated by arrowheads. Molecular weight standards are shown to the left.

FIG. 3. PER forms dimers in vitro. In vitro translations of $^{35}$S-labeled wild-type (lanes 1–3) or $per^L$ version (lanes 4–6) of PER 233–685/H were incubated with 0.005% glutaraldehyde in phosphate buffer for 30 min. at 25° C. They were then immunoprecipitated with anti-HA antibody and analyzed on a 10% SDS-polyacrylamide gel. The arrowhead on the left indicates the cross-linked homodimers of wild-type PER 233–685/H. Unlabeled PER 233–685/H was mixed with either the $^{35}$S-labeled wild-type (lanes 7–9) or $per^L$ version (lanes 10–12) of PER 233–568. They were then cross-linked, immunoprecipitated, and analyzed as lanes 1 to 6. The arrowhead on the right indicates the cross-linked "heterodimers" between PER 233–685/H and PER 233–568. Homodimers of PER 233–685/H and PER 233–568 are not detected in lanes 7–9 since they are either unlabeled or unimmunoprecipitable. "2X" indicates that twice as much of the $^{35}$S-labeled translation products was used as in lanes designated "1X". Molecular weight standards are shown to the left.

FIG. 4 (A). The PAS domain mediates associations between PER and SIM. Schematic representations of full length SIM and PER aligned according to their PAS domains. The PAS and BHLH domains are indicated. In vitro synthesized SIM and PER fragments with a Myc tag (stippled square) or HA tag (black square) are shown. Numbers indicate the first and last amino acids of SIM or PER fragments.

DETAILED DESCRIPTION OF THE PREFERRED EMBODIMENTS

The present invention relates to the discovery of a novel conserved amino acid motif, PAS, found in mammalian and fruitfly proteins. Thus, the invention includes identifying and purifying mammalian proteins that contain PAS domains and can dimerize either with an identical protein or with a different protein that also contains a PAS motif.

The present invention also generally relates to methods for identifying patients with a disease or condition characterized by abnormal PAS-PAS binding affinities. This method is characterized by comparing the sequence of PAS-containing proteins observed in normal individuals to an individual suspected of having the disease or condition. The invention also describes methods for identifying compounds that may promote or interfere with these PAS-PAS binding affinities. The invention further includes identifying and purifying the nucleic acid which encodes the proteins containing a PAS motif. This purified nucleic acid can be expressed in a host cell and various test compounds may be assayed either in vitro or in vivo for the ability to alter the PAS-PAS interactions.

Figure 2A:
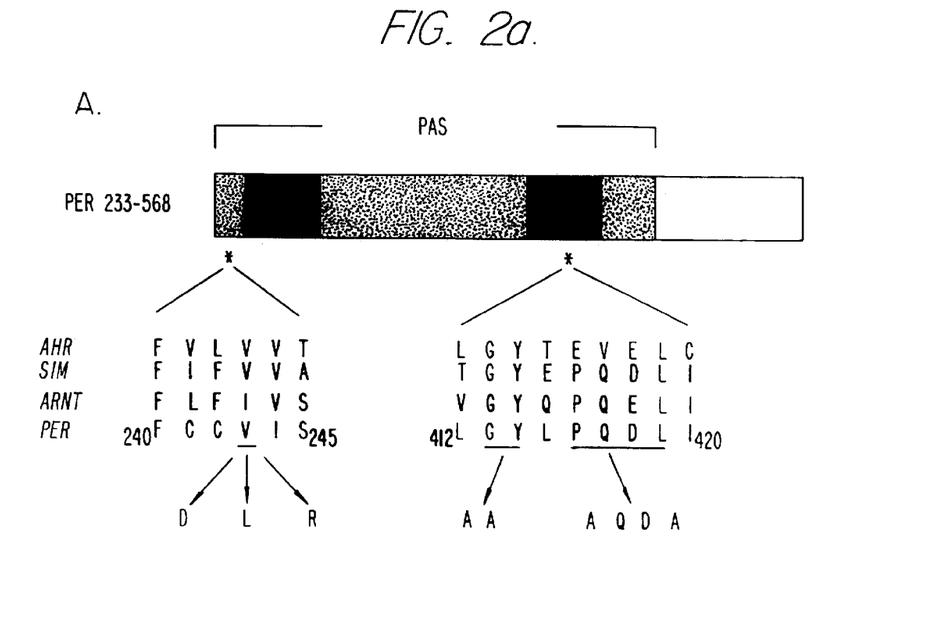
FIG. 2(A). Conserved residues within the PAS domain are important for PER self-association. Diagram of the wild-type and five mutant versions of the PER 233–568 fragment. The PAS domain is indicated at the top and the PAS repeats (dark stippling) are depicted. Two stretches of amino acids that are highly conserved among PAS family members are shown below the asterisks. The first and the last amino acids of each stretch in the PER protein are numbered. The mutated amino acids are underlined, and the corresponding changes are shown as bold letters under the arrows. The mutants are named, from left to right, V/D, V/L, V/R, GY/AA, PL/AA, respectively. The V/D change is the same as that of the original $per^L$ mutation.

FIG. 2A depicts a representation of the PAS domain from proteins found in mammals and fruit flies. The PAS domain is indicated at the top and the PAS repeats are shown as dark stippling. Two stretches of amino acids that are highly conserved are shown below the asterisks. These conserved hydrophobic regions within the PAS domain are believed by applicants to be important for association or binding of proteins containing these PAS motifs. AHR, SIM, ARNT and PER are designations for the four proteins in which the PAS motif has been located, namely the mammalian aryl hydrocarbon receptor, the Drosophila single-minded gene product, the human aryl hydrocarbon receptor nuclear translocator protein and the Drosophila period protein. The one letter symbols following the protein designations are abbreviations for the amino acid found at each location. The cross-references for these symbols and amino acids can be found in Table 1.

A PAS-containing protein is therefore any protein or peptide having a motif which shares a primary sequence homology to the PAS motif of the four proteins described above. Thus, any protein that contains an amino acid sequence identical to, or substantially similar to one of the four PAS-sequences shown in FIG. 2A is a PAS-containing protein. The motif should also be capable of associating, binding or dimerizing either to an identical protein or to another protein containing a PAS motif. Those individuals versed in the art will understand that changes can be made to the amino acid sequence of the PAS motif which do not affect the ability of the PAS motif to associate, bind or dimerize with another protein containing the PAS domain. Thus, any changes which do not affect the ability of the PAS motif to associate, bind or dimerize with another PAS-containing protein do not affect the ability to practice the present invention.

TABLE 1

Abbreviations for amino acids

| Amino Acid | Three-letter abbreviation | One-letter symbol |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Stryer, Biochemistry, W. H. Freeman and Company, New York (3rd. Ed. 1988), p. 21.

Thus, in the first aspect of the present invention, methods for identifying additional mammalian proteins that contain the PAS motif are described. The present methods capitalize on the discovery that PAS is a protein dimerization motif. Novel PAS-containing proteins can be identified in screens by contacting samples believed to contain novel PAS proteins with known proteins that contain the PAS motif under conditions permitting interaction. The known PAS proteins can be derived from any organism, including for example, flies and mammals. Any novel protein that associates with the known PAS proteins can then be sequenced to determine whether, in fact, it contains the PAS motif.

Preferably, applicants employ a two-hybrid yeast system to identify in vivo protein-protein interactions. This method is a modification of known methods reported in Fields, S. and O. Song, Nature (1989); 340:245–248 and Zervos, A. S., et al., Cell (1993); 72:223–232 which are incorporated by reference. The two-hybrid system reported in these papers takes advantage of the properties of the transcriptional activator protein GAL4 from the yeast Saccharomyces cerevisiae. This protein is required for the expression of genes encoding enzymes for galactose utilization and consists of two separable and functionally essential domains: a N-terminal domain that binds to specific DNA sequences; and a C-terminal domain that is necessary to activate transcription.

As described by Fields and Song, the two-hybrid system requires that the GAL4 protein be cleaved into its two functional domains. The N-terminal DNA binding region then is fused to one unit of the subject dimerization protein pair and the C-terminal transcription activating region is fused to the other protein dimer. If the proteins dimerize after introduction into the yeast, the DNA binding and transcription activity regions of GAL4 are brought into close proximity and transcription of the reporter gene is activated. If the proteins do not dimerize, the reporter gene is not transcribed. Thus, a simple system for investigating protein-protein interactions is possible.

The two-hybrid method can be modified to identify new proteins by detecting protein-protein interactions of known proteins with the new protein. In this system cDNA libraries are constructed using methods known in the art from various tissues that are believed to express the proteins of interest. See, e.g., Chien, C. T., et al., *Proc. Nat'l. Acad. Sci. USA* (1991); 88:9578–9582; Dalton and Treisman, *Cell* (1992); 68:597–612. A library that conditionally expresses cDNA-encoded proteins fused to an epitope tag, a nuclear localization sequence and an acidic transcription activation region of GAL4 is introduced into a special yeast strain. That special yeast strain contains a plasmid that directs the synthesis of a construct that includes the DNA binding region of GAL4 and the protein interacting domain of the known protein. The strain also contains a reporter gene, the transcription of which is stimulated if the library encoded protein complexes or dimerizes with the known protein construct. Again, by monitoring the transcription of the reporter gene, new proteins that interact with the known protein may be identified.

In applicant's preferred method, DNA libraries are constructed using methods known in the art from various tissues of interest (e.g., brain tissue will be used to locate potential PAS-containing proteins relevant to behavioral disorders, liver tissue for epithelial cancers, etc.). The library is designed such that cDNA-encoded proteins are fused to an epitope tag, a nuclear localization sequence and the acidic transcription domain from GAL4 and are conditionally expressed.

This library DNA is then introduced into a yeast strain containing a plasmid that expresses a known PAS-containing protein, or only the PAS motif of that protein, fused to the DNA binding region of GAL4. The strain also contains two different reporter genes whose expression is influenced by the GAL4 transcription activating protein. One reporter gene will allow growth of the yeast strain in the absence of leucine. The other reporter gene directs the synthesis of beta-galactosidase and turns the yeast colony blue in the presence of galactose.

By plating a pool of these transformed yeast cells onto galactose-Leu⁻ selection plates, yeast cells containing new proteins that interact with the known PAS protein can be identified. Since these individual yeast colonies only contain a single cDNA-containing plasmid, the relevant cDNA encoding a mammalian protein fragment can be cloned into *E. coli*, amplified, identified and sequenced using methods known in the art to verify that it contains the PAS motif.

The DNA encoding the PAS-containing protein can be separated from other cellular components and purified to a homogenous form using methods known in the art. See, e.g., Chien, C. T., et al., *Proc. Nat'l. Acad. Sci. USA* (1991); 88:9578–9582; Dalton and Treisman, *Cell* (1992); 68:597–612. By isolating and purifying the DNA sequence for the whole gene encoding the PAS-containing protein, the sequence of the bases also may be determined by known methods, such as Maxam and Gilbert, *Proc. Natl. Acad. Sci. USA* (1977); 74:560. The sequence can be used for determination of the amino acid sequence of the protein expressed by the gene. By identifying codons for methionine followed by a sequence which does not have stop codons which prevent expression, one can usually find a single sequence in frame with a methionine codon for defining the gene.

Once the DNA sequence of the mammalian PAS-containing protein is obtained, individuals can be screened to determine the significance of PAS domain functions from changes in the DNA sequence. For example, a library of DNA can be obtained using methods known in the art from individuals who exhibit symptoms of human behavioral disorders, as well as from control (normal) individuals. The PAS domain segments of these individuals can be located and sequenced. Using standard statistical correlation procedures, methods for diagnosing whether a subject individual has a behavioral disorder then readily can be created by comparing the subject individual's PAS domain DNA sequence to a control sequence. See, e.g., Barker, D., et al., *Science* (1987); 236:1100–1102; Wallace, M. R., et al., *Science* (1990); 249:181–186; Li, et al., *Cell* (1992); 69:275–281. This type of analysis also is currently possible to characterize the dioxin receptor and to determine the role of sequence abnormalities of that gene in cancer development. The literature indicates that a particular allele may be inherited at this locus that affects tumor incidence. Knutson, J. D. and A. Poland, *Cell* (1980); 22:27–36; Knutson, J. C. and A. Poland, *Cell* (1982); 30:225–234; Poland, A. et al, *Nature* (1982); 300:271–273; Kellerman, G. et al, *Amer. J. Hum. Genet.* (1973); 25:327–331; Paigen, B. et al, *Amer. J. Hum. Genet.* (1978); 30:561–571; Borresen A. L. et al, *Clinical Genetics* (1981); 19:281–289.

Hybrid DNA technology known in the art also may be employed to obtain expression of purified DNA encoding a PAS-containing protein. The DNA sequence may be restriction mapped and appropriate sites for cleavage defined. In this way, the sequence encoding the PAS-containing protein may be excised and introduced into a vector having appropriate regulatory signals. After introducing the vector into a host cell, the DNA sequence is expressed and purified recombinant human protein containing a PAS region may be obtained using methods known in the art. See, e.g., Zervos, et al., *Cell* (1993); 72:223–232.

Similarly, once the mammalian PAS-containing protein sequences are known, individuals can be screened to determine the significance of changes in the amino acid sequence among individuals. Again, PAS-containing proteins isolated from individuals who exhibit symptoms of behavioral disorders and control individuals can be sequenced and compared. Using the information from this analysis, methods for diagnosing behavioral disorders in subject individuals can easily be devised.

Once novel PAS-containing proteins are identified and isolated, one can then use the protein or subunit peptides as an antigen for the production of antibodies. Antibodies can be prepared using a variety of methods well known in the art. Either monoclonal or polyclonal antibodies may be desired. For polyclonal antibodies, a vertebrate, normally a domestic animal, is hyperimmunized with the antigen and blood collected shortly after repeat immunizations and gamma globulin isolated. For monoclonal antibodies, a small animal is hyperimmunized, the spleen removed and the lymphocytes fused with an appropriate fusing partner. The resulting hybridomas are then grown under limiting dilution and clones providing the desired antibodies selected. The tissues that express novel PAS-containing proteins can then be identified by known procedures of antibody staining or in situ hybridization. See, e.g., Harlow and Lane, *Antibodies A Laboratory Manual*, Cold Spring Harbor Laboratory, 1988 which is incorporated herein by reference.

Various compounds also can be tested to determine the ability of the compound to interfere with PAS-PAS interactions. An in vivo yeast system is utilized and a plasmid is constructed that encodes the PAS-containing proteins of interest. The first protein is comprised of a PAS-containing protein, or a subunit containing the PAS-motif, fused to the DNA binding domain of the GAL4 protein. The second protein is comprised of a second PAS-containing protein whose interaction with the first PAS-containing protein is sought to be investigated, fused to the transcription activating domain of the GAL4 protein. The third protein is a reporter protein whose transcription is influenced by GAL4 as described above.

Once this yeast strain is prepared, it can be grown in large quantities. Drug candidates can then be screened by contacting the host cell with the test compound and assessing the ability of the test compound to interfere with the PAS-PAS interaction.

An in vitro assay may also be employed to screen drug candidates. To study the stoichiometry of the PER protein oligomers in vitro, applicants have designed a chemical cross-linking and immunoprecipitation procedure. This in vitro procedure is described in detail in Example 3 below.

This in vitro procedure can be modified to screen drug candidates by introducing the test compounds before the PAS-containing proteins are cross-linked by glutaraldehyde. Any compounds which inhibit or promote this cross-linking reaction are then candidates for further research.

The following examples are provided for illustration of the ability of the PAS motif to mediate protein-protein interactions and are not intended to limit the scope of the invention.

EXAMPLE 1

Co-Immuno Precipitation Assay

To test whether the PAS domain can mediate protein-protein interactions, we designed a co-immunoprecipitation assay: per cDNA encoding PER 233–685/H was generated by the polymerase chain reaction (PCR) from the full length per cDNA (pSP65ATper). Citri, Y., et al., *Nature* (1987); 326:42–47. The 5' primer contains, from 5' to 3', an XbaI site, an ATG codon and nucleotides 697 to 717 of per cDNA; the 3' primer contains, from 5' to 3', an XbaI site, a TAG stop codon, the sequence corresponding to the HA peptide (YPYDVPDVASL) (Kolodziej, P. A., et al., *Meth. Enzymol.* (1991), SEQ. ID. NO. 9; 194:508–519), and nucleotides 2052 to 2035 of per cDNA. The PCR products were inserted into the pBluescript KS(-) vector (Stratagene) at the XbaI site such that the per cDNA was under the control of the T7 promoter (pBSC2H), and the construct was verified by DNA sequencing.

cDNAs coding for PER 295–685/H and PER 391–685/H were obtained by PCR using pBSC2H as a template. The 5' primers contain a T7 promoter, the 5' leader and ATG from the human β-globin gene (Schindler, U., et al., *EMBO J.* (1992); 11:1261–1273), and nucleotides 883 to 902 (PER 295–685/H), or nucleotides 1174 to 1193 (PER 391–685/H) of the per cDNA; the 3' primer for both cDNAs contains nucleotides 806 to 787 of the (+) strand of the pBluescript (KS-) vector. More than two independent PCR products for each cDNA were used for analysis and gave identical results in the experiments described below. The cDNA for PER 233–568 was generated by linearizing pBSC2H with SmaI at nucleotide 1704 of per cDNA.

Approximately 1 μg of DNA was used for in vitro transcription. RNAs were translated using a rabbit reticulocyte lysate in the presence of $^{35}$S-labeled methionine according to the manufacturer's instructions (Promega). 1 μl of translation reaction was used to measure TCA-precipitable cpm. Translation products of approximately equal cpm were mixed and incubated at 37° C. for 30 min. Typically ca. $5\times10^4$ cpm of a translation or of a mixing reaction were analyzed by SDS-PAGE. For immunoprecipitation approximately 5-fold more material was diluted in 250 μl of ice cold HND buffer (20 mM HEPES, 100 mM KCl, 10% glycerol, 0.4% NP-40, 5 mM EGTA, 5 mM EDTA, 100 μg/ml BSA, 1 mM DTT, pH 7.4). This and subsequent procedures were done at 4° C. The incubation mixture was first pre-cleared by adding 7 μl of Gamma-Bind Plus Sepharose (Pharmacia), followed by 10 min. rocking. After centrifugation, the supernatant was transferred and incubated with 2 μl of monoclonal antibody 12CA5 for 2 h. 10 μl of Gamma-Bind Plus were then added with further incubation for 1 h. Samples were washed 3 times with HND buffer. They were then heated to 95° C. for 5 min. in SDS sample buffer, centrifuged for 2 min. and electrophoresed by SDS-PAGE on a 12% gel. The gels were fixed, amplified and fluorographed.

Figure 1A:
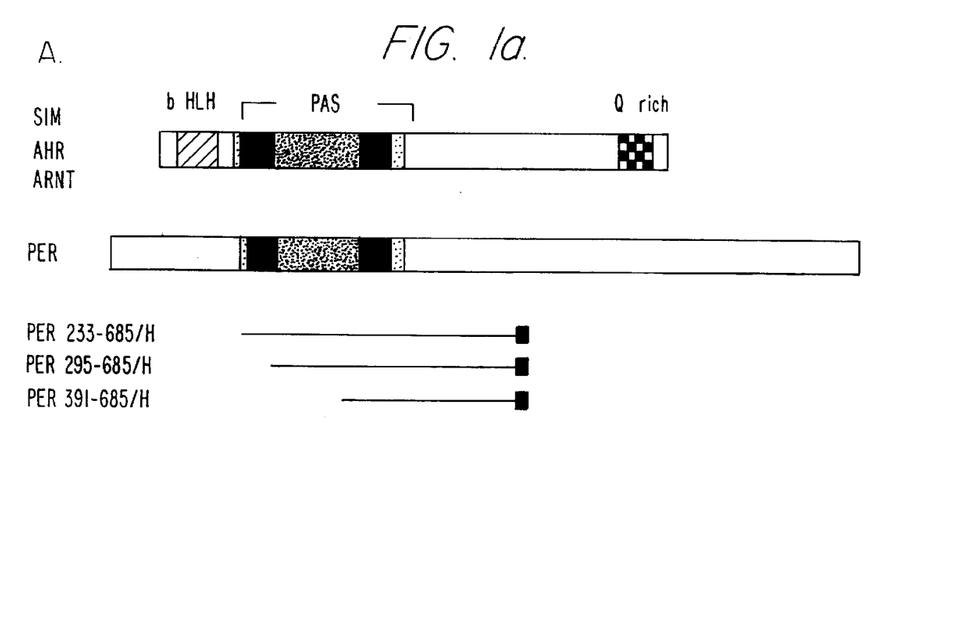
FIG. 1(A). The PAS domain mediates PER protein self-association in vitro. (upper) Schematic representation of the BHLH-PAS proteins (SIM, AHR and ARNT) and the full-length PER protein. BHLH motif, PAS domain, PAS repeats (dark stippling), and glutamine rich (Q rich) region are indicated. (lower) in vitro synthesized PAS-containing PER fragments with and without the hemagglutinin (HA) epitope (black square). Numbers are the first and last amino acids of the PER fragment.
Figure 1B:
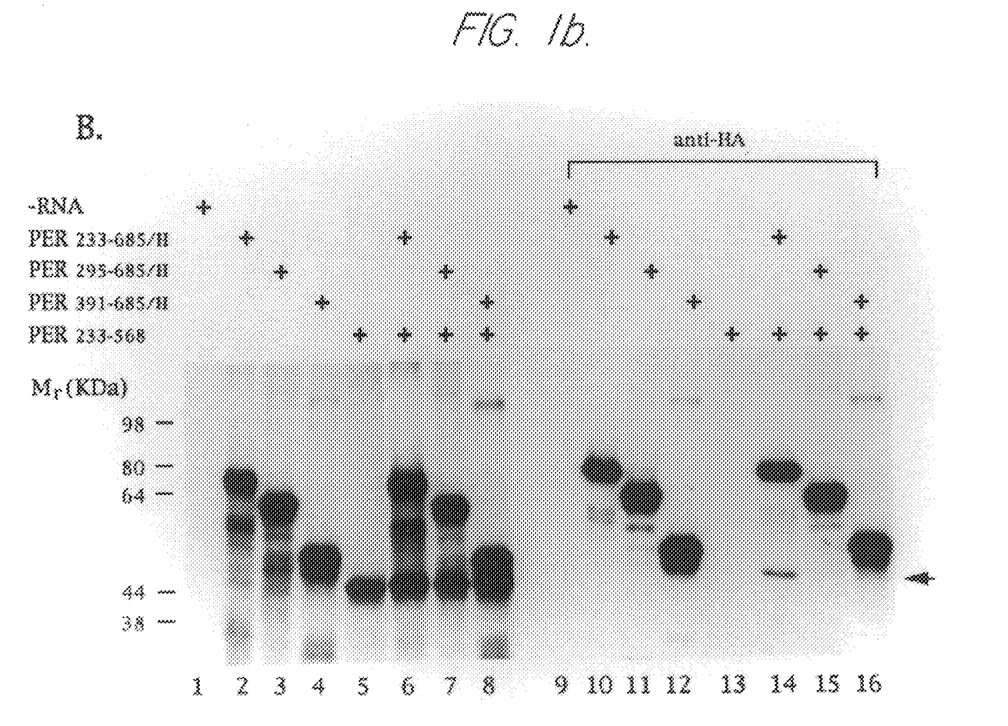
FIG. 1(B). PER fragments in (A) were trans-lated in vitro. Single or mixed translation products were analyzed on a 12% SDS-polyacrylamide gel, either directly (left) or after immunoprecipitation with monoclonal antibody 12CA5 directed against the hemagglutinin peptide (anti-HA, right). The co-immunoprecipitated fragment (PER 233–568) is indicated by an arrow. Molecular weight standards are indicated to the left.

Thus, PER fragments containing complete or truncated PAS regions were synthesized in vitro, either with or without a hemagglutinin epitope (HA tag) at the C-terminus (FIG. 1A). Without an HA tag, PER 233–568 did not react with the anti-HA antibody 12CA5 (FIG. 1B, compare lanes 10–12 with lane 13). It was, however, immunoprecitated after mixing with PER 233–685/H (FIG. 1B, lane 14), indicating that the two polypeptides associate in vitro. 10–15% of PER 233–568 co-immunoprecipitated with PER 233–685/H when they were mixed in an approximately 1:1 molar ratio (based on four experiments) This is an underestimate of PER self-association since PER 233–568/PER 233–568 associations are not detectable in the assay and the association conditions may not be optimal. Full length PER protein also associated with PER 233–685/H (data not shown). Significantly, the immunoprecipitation of PER 233–568 with PAS deletion fragments was greatly reduced (FIG. 1, lanes 15 and 16), indicating that the PAS domain is necessary for PER self-association in vitro.

EXAMPLE 2

Site-Directed Mutagenesis of the PAS Motif Decreases PER Self-Association

To support the above observations, conserved amino acids in the PAS domain were mutated, and the association of the mutant polypeptides with wild-type PER fragments was assayed (FIG. 2). To generate amino acid substitutions, site-directed mutagenesis (Amersham Kit) was carried out with pBSC2H as template and verified by DNA sequencing. These mutant pBSC2H templates were linearized with SmaI to obtain cDNAs for various mutant PER 233–568 fragments. In vitro translations and immunoprecipitations were performed as described in Example 1.

Figure 2B:
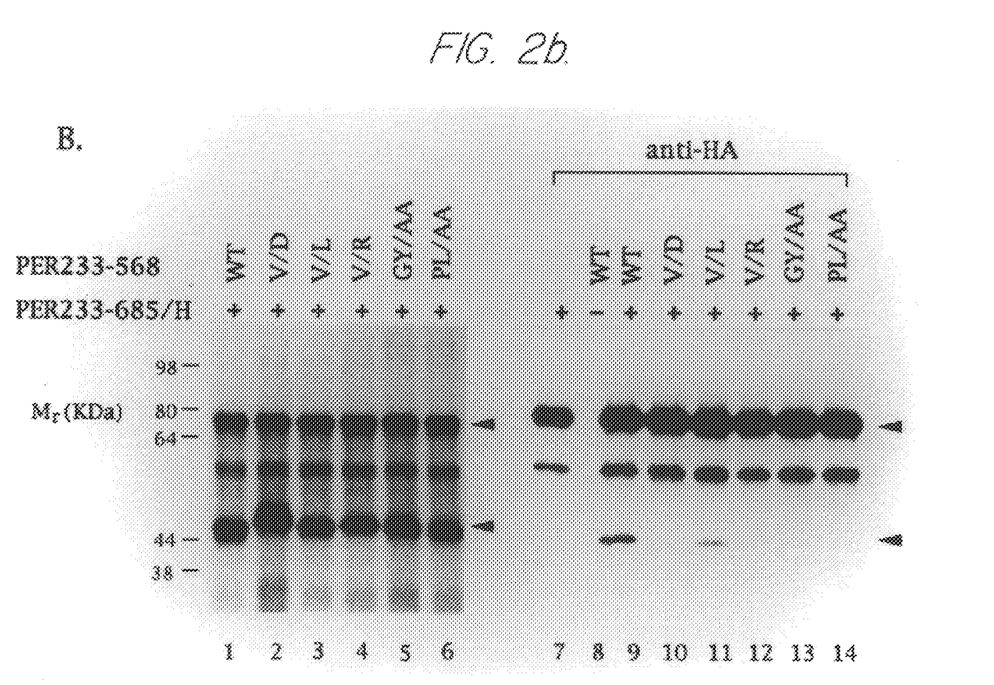

Of particular interest was the valine at position 243 (V243), which lies in a conserved hydrophobic region just N-terminal to the first PAS repeat (FIG. 2A). In the classical per mutation, which gives rise to 29 h circadian rhythms, V243 is mutated to aspartic acid (D243). Konopka, R. J., et al., *Proc. Natl. Acad. Sci. USA* (1971); 68:2112–2116; Yu, Q., et al., *Proc. Natl. Acad. Sci. USA* (1987); 84:784–788; Jackson, R. F., et al., *Nature* (1986); 320:185–188. The sequence of PER 233–685 was modified by site-directed mutagenesis to change V243 to D243 as well as to leucine and arginine (FIG. 2A). Another highly conserved stretch of amino acids in the second PAS repeat was also mutated (FIG. 2A). With one exception, all of the mutations resulted in a significant reduction in co-immunoprecipitation with wild-type PER 233–685/H (FIG. 2B, lanes 9–14). The original per$^L$ (V/D) mutation showed the most severe phenotype (FIG. 2B, compare lanes 9 and 10), a ca. 7-fold reduction in association with PER 233–685/H (based on three experiments). It also resulted in a slower migration on SDS-polyacrylamide gel, suggestive of a substantial structural change in the protein fragment (FIG. 2B, compare lanes 2 and 1). A further decrease in PER self-association was observed when both PER fragments carried the per$^L$ mutation (data not shown; also see FIG. 3). Only the conservative change of V243 to leucine 243 (V/L) resulted in a mild reduction in the co-immunoprecipitation assay (FIG. 2B, lane 11). These observations strengthen the conclusion that the PAS domain engages in PAS-PAS associations.

EXAMPLE 3

Chemical Cross-Linking and Immunoprecipitation Procedure

To study the stoichiometry of the PER protein oligomers in vitro, we designed a chemical cross-linking and immunoprecipitation procedure. Approximately 1×10$^5$ cpm of $^{35}$S-labeled in vitro translated PER 233–685/H were incubated in a final volume of 40 μl in the presence of 0.005% glutaraldehyde in 0.1 M phosphate buffer (pH 7.4) at 25° C. for 30 min. The cross-linking reactions were terminated by adding 2 M Tris (pH 7.5) to a final concentration of 100 mM. Samples were subsequently diluted into 250 μl of HND buffer and immunoprecipitated as described in Example 1. To produce cold PER 233–685/H, in vitro translations were carried out with complete amino acid mixture without radio-labeled methionine. Unlabeled (cold) PER 233–685/H was then mixed with $^{35}$S-labeled PER 233–568 at 37° C. for 30 min. Further cross-linking and immunoprecipitation procedures were performed as described in Example 1.

Figure 3:
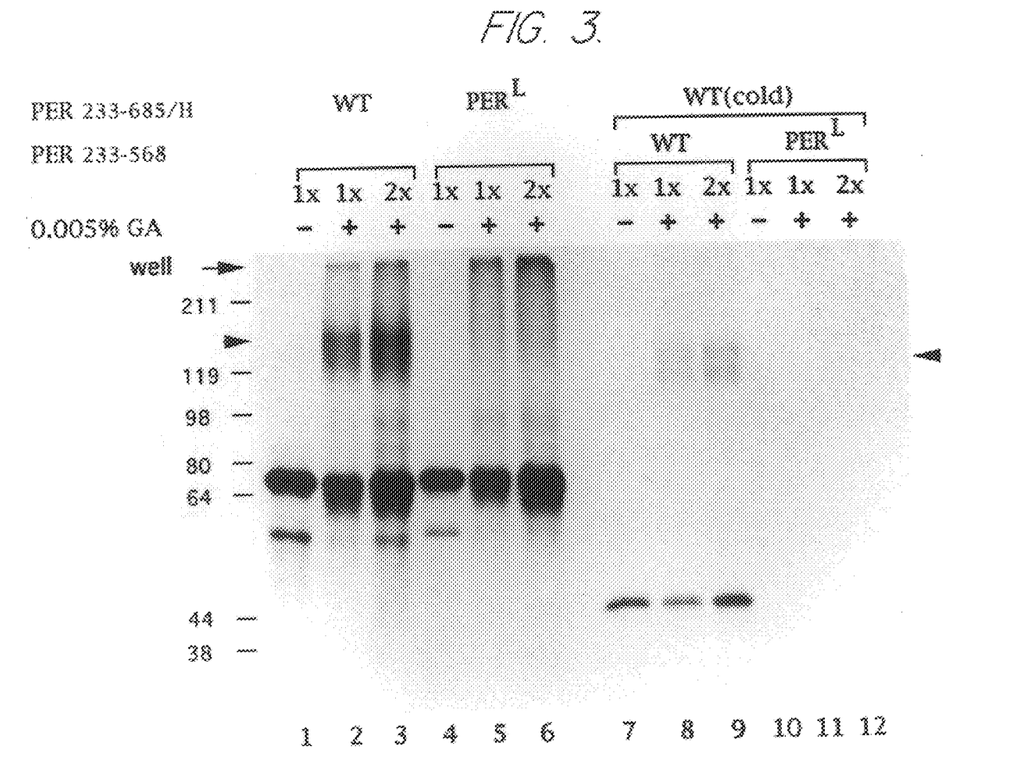

In vitro translation of wild-type (FIG. 3, lanes 1 to 3) or per$^L$ mutant (FIG. 3, lanes 4 to 6) versions of PER 233–685/H were incubated with glutaraldehyde to produce covalent cross-links, immunoprecipitated with anti-HA antibody and analyzed by SDS-PAGE. After incubation, only the wild-type fragment gave rise to dimerized cross-linked products that migrated as a doublet at ca. 140–160 kD (FIG. 3, compare lanes 2 and 3 to lanes 5 and 6; doublet indicated by arrowhead on the left; monomers are ca. 75 kD polypeptides, lanes 1 and 4). This doublet most likely represents two differentially cross-linked forms of the dimers. To ensure that two PAS-containing proteins can dimerize, an additional cross-linking-immunoprecipitation experiment was carried out in which non-radioactive PER 233–685/H (cold) was mixed with the smaller, 45 kD radiolabeled PER 233–568 (either the wild-type or the PERL version). As the assay only detects radioactive oligomers that also contain an HA epitope, the formation of radioactive dimers must result from an associate between the cold and radioactive polypeptides. An appropriately sized doublet (ca. 110–130 kD; indicated by the arrowhead on the right) was detected only with the wild-type PER fragment (FIG. 3, compare lanes 8 and 9 to 11 and 12), indicating that the PAS domain dimerizes in vitro and that the PER$^L$ fragment is at least 10 times less efficient than its wild-type counter-part in this dimerization assay.

EXAMPLE 4

PER Associates with other PAS-Containing DNA Proteins

Figure 4A:
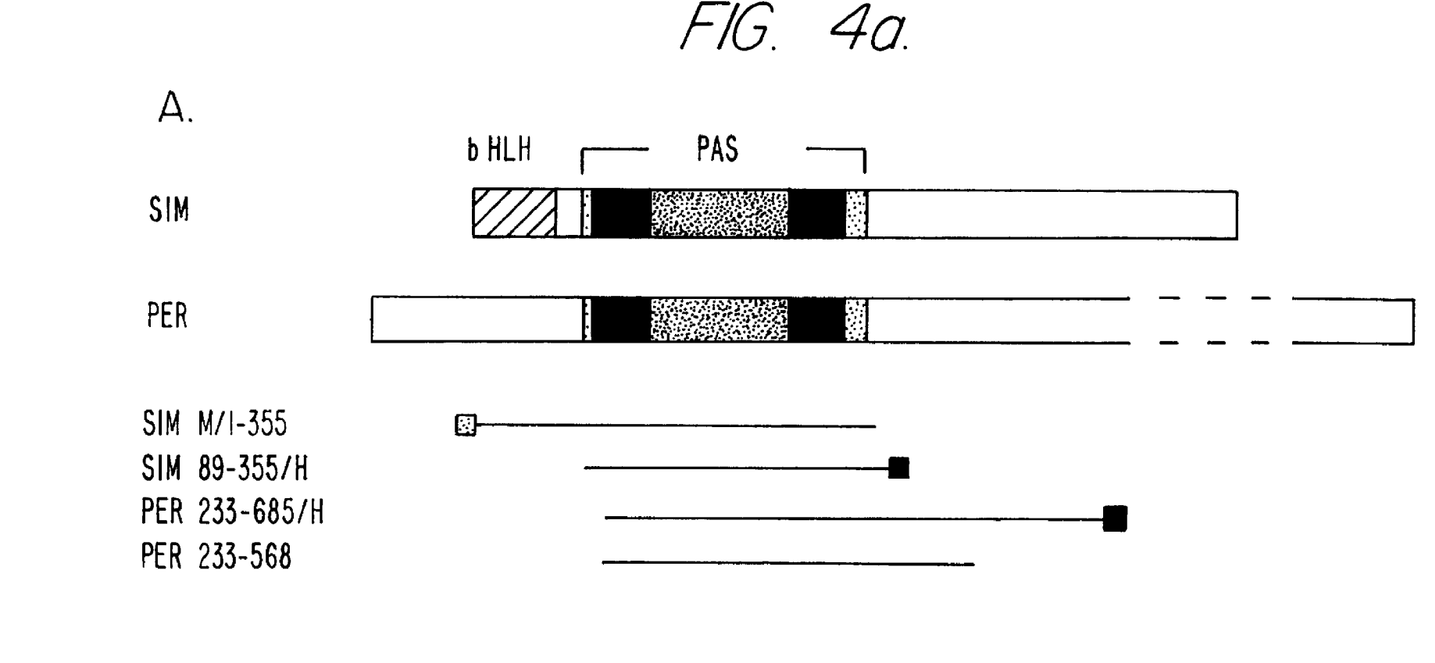
Figure 4B:
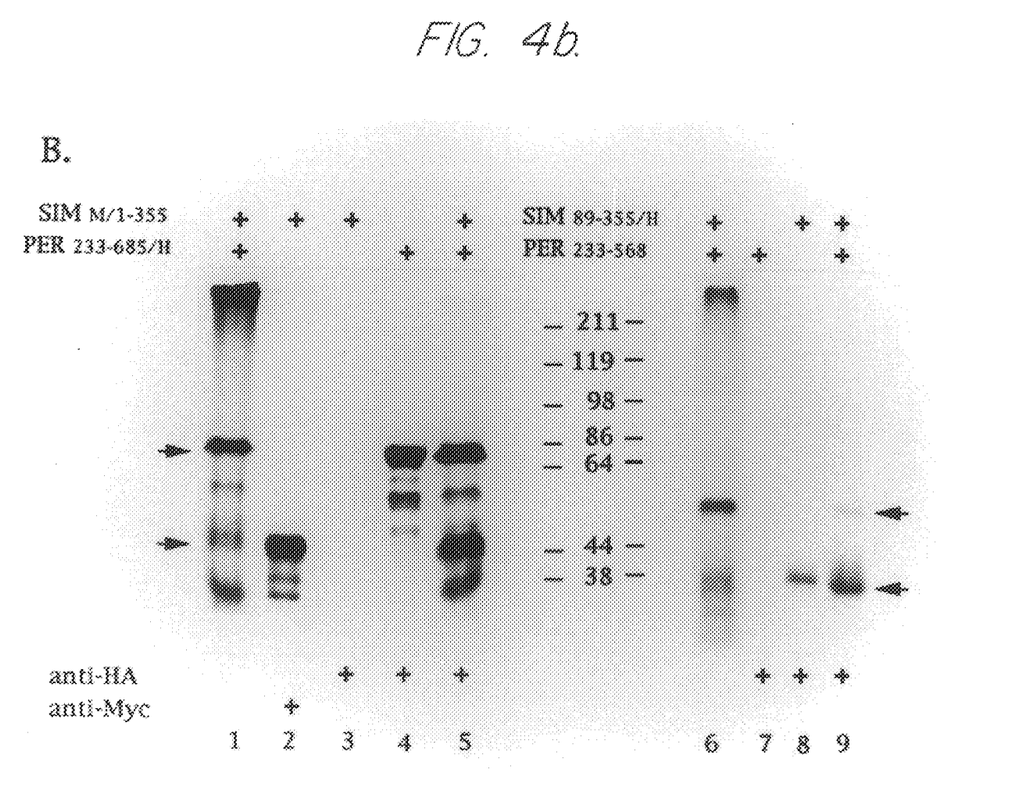
FIG. 4(B). SIM and PER fragments were in vitro translated; single or mixed translation products were analyzed on a 10% SDS-polyacrylamide gel, either directly (lanes 1 and 6) or after immunoprecipitation with anti-Myc or anti-HA antibody. Arrows on the left indi-cate the positions of PER 233–685/H (upper) and SIM M/1–355 (lower). Arrows on the right indicate PER 233–568 (upper) and SIM 89–355/H (lower).

The apparent contradiction between PER's possible role in gene regulation and the absence of an obvious DNA binding domain and DNA binding activity (data not shown) can be reconciled by proposing that it regulates transcription through interactions with other PAS-containing DNA binding proteins. To address this possibility, we tested whether PER can associate with other PAS family members that contain DNA binding regions. A SIM fragment containing the BHLH and PAS domain with a Myc epitope at its N-terminus (SIM M/1–355) was translated in vitro (FIG. 4A). This fragment was immunoprecipitated by the anti-Myc antibody 9E10, but not by the anti-HA antibody 12CA5 (FIG. 4, lanes 2 and 3). When mixed with PER 233–685/H, it was co-precipitated by the anti-HA reagent (FIG. 4B, lanes 1 and 5), indicating that the two fragments can associate in vitro. To show that the SIM PAS domain was sufficient for the association, a SIM fragment containing only the PAS domain and an HA tag (SIM 89–355/H) was used (FIG. 4A). The anti-HA antibody precipitated PER 233–568 along with SIM 89–355/H only when the two fragments were mixed (FIG. 4, lanes 6–9). The PER PAS domain can also mediate a similar association between protein fragments of PER and ARNT, a subunit of the mammalian dioxin receptor complex. Taken together, the observations demonstrate that the PAS domain is a novel protein-protein interaction domain.

In the known BHLH-PAS proteins from both mammals and flies, it is intriguing that PAS domains are located just C-terminal to the BHLH motifs, similar to the leucine zipper (LZ) domain in the BHLH-LZ protein family (e.g., MYC and MAX). Blackwood, E. M., *Science* (1991); 251:1211–1217. The BHLH-PAS proteins thus may represent a new subfamily of BHLH proteins. As the dioxin binding region of AHR is apparently localized to the PAS domain. (Burbach, K. M., et al., *Proc. Natl. Acad. Sci. USA* (1992); 89:8185–8189), there may be some relationship between ligand-binding and the PAS mediated protein-protein interaction (i.e., heterodimer formation between AHR and ARNT), not unlike what has been observed for the steroid hormone receptors. Forman, B. M., et al., *Mol. Endocrinol.* (1990); 4:1293–1301; Fawell, S. E., et al., *Cell* (1990); 60:953–962. In addition, it is possible that unknown ligands participate in the regulation of PER or SIM function in Drosophila.

The foregoing is intended to be illustrative of the present invention, but not limiting. Numerous variations and modifications may be effected without departing from the true spirit and scope of the novel concepts of the invention.

We claim:

1. Method for identifying a molecule potentially useful as a therapeutical molecule by altering the interaction of AH receptor protein and Arnt protein through their PAS domains, comprising the steps of:

contacting a test molecule with isolated PAS domains from said AH receptor protein and Arnt protein; and assessing the ability of the test molecule to alter the interaction of said PAS domains as an indication of a potentially useful therapeutic molecule which alters the interaction of said AH receptor protein and Arnt protein through their PAS domains.

2. The method of claim 1 wherein assessing the ability of the test molecule to alter the interaction of said PAS domains comprises:

incubating the test molecule with said PAS domains under conditions that would allow said PAS domains to interact in the absence of the test molecule;

contacting the test molecule and said PAS domains with a chemical cross-linking agent; and assessing whether said PAS domains have been cross-linked.

3. The method of claim 2 wherein the chemical cross-linking agent is glutaraldehyde.

4. The method of claim 3 wherein assessing whether said PAS domains have been cross-linked is performed by gel electrophoresis.

5. Method for identifying a molecule useful for altering the interaction of proteins through PAS domains, comprising the steps of:

contacting a test molecule with isolated PAS domains from said proteins containing a PAS domain; and assessing the ability of said test molecule to alter the interaction of said PAS domains as an indication of a molecule useful for altering the interaction of said proteins through said PAS domain.

* * * * *